United States Patent [19]

Biftu et al.

[11] Patent Number: 5,011,847
[45] Date of Patent: Apr. 30, 1991

[54] 2,5-DIARYL TETRAHYDROFURANS AND ANALOGS THEREOF AS PAF ANTAGONISTS

[75] Inventors: Tesfaye Biftu, Parlin; Mitree M. Ponpipom, Branchburg; Nirindar N. Girotra, Parlin, all of N.J.

[73] Assignee: Merck & Co., Inc., Rahway, N.J.

[21] Appl. No.: 362,909

[22] Filed: Jun. 8, 1989

[51] Int. Cl.$^5$ .................. C07D 405/04; A61K 31/44
[52] U.S. Cl. .................. 514/336; 546/283; 549/497; 549/498; 549/499; 549/500; 549/501; 549/502
[58] Field of Search ............... 549/497, 498, 499, 500, 549/501, 502; 546/283; 514/336

[56] References Cited

U.S. PATENT DOCUMENTS

| | | | |
|---|---|---|---|
| 3,769,350 | 10/1973 | Perry et al. | 568/8 |
| 4,539,332 | 9/1985 | Biftu et al. | 514/461 |
| 4,595,693 | 5/1986 | Biftu et al. | 514/461 |
| 4,757,084 | 7/1988 | Biftu et al. | 514/438 |

FOREIGN PATENT DOCUMENTS

| | | | |
|---|---|---|---|
| 0154887 | 2/1985 | European Pat. Off. | 549/77 |
| 0144804 | 6/1985 | European Pat. Off. | 549/502 |
| 0199324 | 10/1986 | European Pat. Off. | 549/502 |
| 0217204 | 4/1987 | European Pat. Off. | 549/502 |

OTHER PUBLICATIONS

Chem. Abstracts, vol. 42, Abstract 5836e (1948).
Chem. Abstracts, vol. 79, Abstract 136925u (1973).
Chem. Abstracts, vol. 81, Abstract 135662k (1974).
Chem. Abstracts, vol. 83, Abstract 8676g (1975).
Chem. Abstracts, vol. 86, Abstract 16468v (1977).
Chem. Abstracts, vol. 90, Abstract 54746z (1979).
Chem. Abstracts, vol. 96, Abstract 122588a (1982).
Biftu, T., Hazra, G. B., Steveson, R., and Williams, J. R., Synthesis of Ligans, 2,3-Diaroylbutanes, J. Chem. Soc., pp. 1147-1150 (1978).
Biftu, T., Hazra, G. B., Steveson, R., Synthesis of (+)-Deoxyschizandrin, J. Chem. Soc., pp. 2276-2281 (1979).
Hwang, S. B., Lam, M. H., Biftu, T., Beattie, T. R., Asghen, T. Y., Trans-2,5-bis-(3,4,5-Trimethoxyphenyl) Tetrahydrofuran, J. Biol. Chem., vol. 260, No. 29, pp. 15639-15645 (Dec. 1985).
Sarkanen, K. V. and Wallis, A. F. A., Oxidative Dimerization's of (E)- and (Z)-Isoeugenol (2-Methoxy-4-Propenylphenol) and (E)- and (Z)-2,6-Dimethoxy-4-Propenyl-Phenol, J. Chem. Soc., Perkin transactions, pp. 1869-1878 (1973).
Stevenson, R., Williams, J. R., Synthesis of Tetrahydrofuran Lignans, (+)-Galbelgin and (+)-Grandisin, Tetrahedron, vol. 33, pp. 285-288 (1977).

Primary Examiner—Alan L. Rotman
Attorney, Agent, or Firm—Curtis C. Panzer; Hesna J. Pfeiffer; Joseph F. DiPrima

[57] ABSTRACT

The present invention is directed to a specifically substituted tetrahydrofuran of the formula (I)

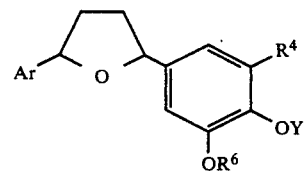

wherein Ar is a pyridyl, dimethoxy-pyridyl or a dimethoxy-pyrazinyl group, $R^4$ is an alkylthio, alkylsulfinyl or alkylsulfonyl containing group, Y is an alkyl or substituted alkyl group, $R^6$ is an alkyl or a substituted alkyl and the substituents at positions 3, 4 and 5 are acyclic.

11 Claims, No Drawings

2,5-DIARYL TETRAHYDROFURANS AND ANALOGS THEREOF AS PAF ANTAGONISTS

BACKGROUND OF THE INVENTION

Platelet activating factor (PAF) has recently been identified as an acetyl glyceryl ether phosphorylcholine (AGEPC), i.e., 1-0-hexadecyl/ octadecyl-2-acetyl-sn glyceryl-3-phosphorylcholine (Hanahan D. J., et al., *J. Biol. Chem.* 255:5514, 1980). Even before its chemical identification, PAF had been linked to various biological activities and pathways making it one of the important mediators responsible for a variety of physiological processes including activation or coagulation of platelets, pathogenesis of immune complex deposition, smooth muscle contraction, inflammation, hypotension, shock, pain, edema as well as respiratory, cardiovascular and intravascular alterations. Since these physiological processes are in turn associated with a large group of diseases, for example, inflammatory disease, cardiovascular disorder, hypotension, shock, psoriasis, allergic and skin diseases, asthma, lung edema, peptic or stomach ulcer, dental pain, and adult respiratory distress syndrome, more and more scientific investigation has been focused on the search of a PAF antagonist or inhibitor for treating or preventing these common diseases.

The compounds of the present invention are specific PAF antagonists. They are similar to a subclass of compounds called lignans which characteristically contain two phenylpropyl groups bonded at the β-carbon. Tetrahydrofuran (THF) derivatives can exist in eight different stereochemical configurations as shown in Scheme I.

Scheme I

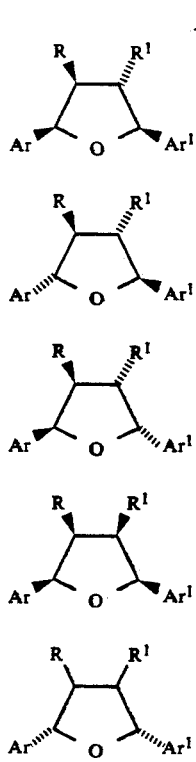

-continued
Scheme I

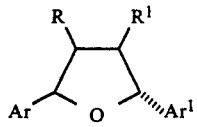
(6)

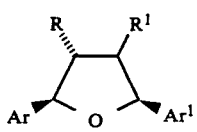
(7)

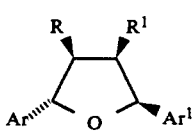
(8)

We have been able to prepare all the possible isomers of the tetrahydrofuran lignan analogs with different substituents and found that activity is stereospecific.

Accordingly, the present invention is directed to the preparation of the most potent isomers of known or novel tetrahydrofuran derivatives as PAF antagonists and use them for the treatment of various diseases including prevention of platelet aggregation, hypotension, inflammation, asthma, lung edema, adult respiratory distress syndrome, various shock syndromes, cardiovascular disorders and other related skeletal-muscular disorders graft-host rejection, nephritis, pancreatitis, and lupus.

The present invention is also directed to acceptable pharmaceutical compositions containing one or more of the tetrahydrofuran derivatives and/or analogs as the active ingredient. As PAF antagonists, these novel compositions should be effective in the treatment of various skeletal-muscular related diseases.

The present invention is also directed to a method of treatment comprising the administration of a therapeutically sufficient amount of these PAF antagonists to a patient suffering from various skeletal-muscular disorders including inflammation, e.g., osteoarthritis, rheumatoid arthritis and gout, hypotension, shock, psoriasis, allergic or skin diseases, asthma, pain especially dental pain, peptic or stomach ulcer, lung edema, adult respiratory distress syndrome or cardiovascular disorders graft-host rejection, nephritis, pancreatitis, and lupus.

BRIEF DESCRIPTION OF THE INVENTION

The present invention is directed to a specifically substituted tetrahydrofuran of the formula (I)

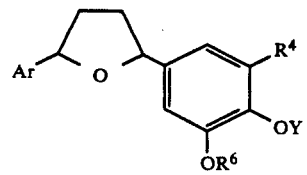

wherein Ar is a pyridyl, dimethoxy-pyridyl or a dimethoxy-pyrazinyl group, $R^4$ is an alkylthio, alkylsulfinyl or alkylsulfonyl containing group, Y is an alkyl or substituted alkyl group, $R^6$ is an alkyl or a substituted alkyl and the substituents at positions 3,4 or 5 are acyclic.

DETAILED DESCRIPTION OF THE INVENTION

The present invention is directed to compounds of the following structural formula (I):

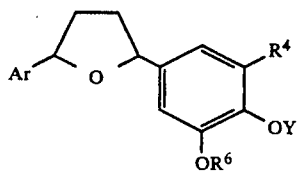

or a pharmaceutically acceptable salt thereof wherein:

Ar is selected from the group consisting of pyridyl, dimethoxypyridyl and dimethoxypyrazinyl;

$R^4$ is $S(O)_n R^2$ in which n is 0, 1 or 2 and $R^2$ is selected from the group consisting of
  (a) $C_{2-6}$alkyl,
  (b) Substituted $C_{1-6}$alkyl wherein the substituent is selected from the group consisting of hydroxy, amino, N-$C_{1-4}$ alkylamino, and N,N-di-$C_{1-4}$alkylamino, and
  (c) $C_{1-6}$alkylcarbonyl-$C_{1-6}$alkyl;

Y is selected from the group consisting of
  (a) $C_{1-12}$alkyl,
  (b) $C_{1-6}$hydroxyalkyl,
  (c) $C_{1-6}$alkylcarbonyl-$C_{1-6}$alkyl, and
  (d) amino-$C_{1-6}$alkyl;
  (e) N-substituted or N,N-disubstituted amino-$C_{1-6}$alkyl wherein the substituents are each individually $C_{1-6}$alkyl;

$R^6$ is selected from the group consisting of
  (a) substituted $C_{1-6}$alkyl wherein the substituent is selected from the group consisting of hydroxy, amino, N-$C_{1-4}$alkylamino, N,N-di-$C_{1-4}$alkylamino, and —O—$R^{10}$, wherein is $R^{10}$ is
    (1) —$PO_2(OH)^- M^+$ wherein $M^+$ is a pharmaceutically acceptable cation.
    (2) —$SO_3$—$M^+$, or
    (3) —$C(O)(CH_2)_2$—$CO_2$—$M^+$,
  (b) $C_{1-6}$alkylcarbonyl-$C_{1-6}$alkyl, and
  (c) $C_{1-6}$carboxyalkyl.

As will be understood by those skilled in the art, pharmaceutically acceptable salts include, but is not limited to salts with inorganic acids such as hydrochloride, sulfate, phosphate, diphosphate, hydrobromide, and nitrate or salts with an organic acid such as malate, maleate, fumarate, tartrate, succinate, citrate, acetate, lactate, methanesulfonate, p-toluenesulfonate, palmoate, salicylate and stearate. Similarly pharmaceutically acceptable cations include, but is not limited to sodium, lithium, potassium, calcium, aluminum and ammonium.

Illustrating the invention is the class of compounds of the formula (I) wherein the substituents at positions 2 and 5 of the tetrahydrofuran are in a trans relationship to one another, and Y is
  (a) $C_{1-6}$alkyl, or
  (b) $C_{1-4}$alkylcarbonyl-$C_{1-4}$alkyl.

A subclass of these compounds is the compounds of formula (I) wherein n is 2, and $R^2$ is selected from the group consisting of
  (a) Substituted $C_{1-6}$alkyl wherein the substituent is selected from the group consisting of hydroxy, amino, N-$C_{1-4}$alkylamino, and N,N-di-$C_{1-4}$alkylamino, and
  (b) $C_{1-4}$alkylcarbonyl-$C_{1-4}$alkyl.

A smaller subclass of these compounds is the compounds of formula (I) wherein:

$R^6$ is
  (a) substituted $C_{1-6}$alkyl wherein the substituent is selected from the group consisting of hydroxy, amino, N-$C_{1-4}$alkylamino, N,N-di-$C_{1-4}$alkylamino, and —O—$R^{10}$, wherein $R^{10}$ is
    (1) —$PO_2(OH)^- M^+$ wherein $M^+$ is a pharmaceutically acceptable cation,
    (2) —$SO^-·M^+$, or
    (3) —$C(O)(CH_2)_2$—$CO^-_2 M^+$, and
  (b) $C_{1-6}$alkylcarbonyl-$C_{1-6}$alkyl.

A still smaller subclass of these compounds is the compounds of formula (I) wherein Y is n-propyl or 2-oxopropyl.

Exemplifying this subclass are those compounds of the formula (I) which are:
  (a) trans-2-[3-n-propylsulfonyl-4-n-propoxy-5-(2-oxopropoxy) phenyl]-5-(3-pyridyl) tetrahydrofuran,
  (b) trans-2-[3-n-propylsulfonyl-4-n-propoxy-5-(2-oxopropoxy) phenyl]-5-[5-(2,3-dimethoxy) pyridyl]tetrahydrofuran,
  (c) trans-2-[3-n-propylsulfonyl-4-n propoxy-5-(2-hydroxypropoxy) phenyl]-5-[5-(2,3-dimethoxy)-pyridyl]tetrahydrofuran,
  (d) trans-2-[3-(2-Hydroxypropyl)sulfonyl-4-n-propoxy 5-(2 oxopropoxy)phenyl]-5 [5-(2,3-dimethoxy)pyridyl]tetrahydrofuran,
  (e) trans-2-[3 (2-Hydroxypropyl)sulfonyl 4-n propoxy-5-(2 hydroxypropoxy) phenyl]-5-[5-(2,3-dimethoxy)pyridyl]tetrahydrofuran,
  (f) trans-2-[3-(2 Hydroxypropyl)sulfonyl 4-n propoxy 5-(3 hydroxypropoxy) phenyl]-5-[5 (2,3 dimethoxy)pyridyl]tetrahydrofuran,
  (g) trans-2-[3 (2-Hydroxypropyl)sulfonyl 4-n propoxy 5-(2 hydroxyethoxy) phenyl]5-[5-(2,3-dimethoxy)pyridyl]tetrahydrofuran,
  (h) trans-2-[3 (2-Oxopropyl)sulfonyl-4-n-5-(3-hydroxypropoxy) phenyl]-5-[5-(2,3 dimethoxy)pyridyl]tetrahydrofuran,
  (i) trans-2-[3-n-propylsulfonyl-4-n-propoxy-5-(2-oxopropoxy) phenyl]-5-[6-(2,3-dimethoxy) pyrazyl]tetrahydrofuran,
  (j) trans-2-[3-n-propylsulfonyl-4-n propoxy-5-(2-hydroxypropoxy) phenyl]-5-[6-(2,3-dimethoxy) pyrazyl]tetrahydrofuran, and
  (k) trans-2-[3-(2-Hydroxypropyl)sulfonyl-4-n-propoxy-5-(2-oxopropoxy) phenyl]-5-[6-(2,3-dimethoxy)pyrazyl]tetrahydrofuran,
  (l) trans-2-[3-(2-Hydroxypropyl)sulfonyl 4-n-propoxy-5-(3-hydroxypropoxy) phenyl]-5-[6-(2,3-dimethoxy)pyrazyl]tetrahydrofuran, or a stereochemical isomer thereof in the (2S,5S) configuration.

The compounds of formula I may be prepared by the methods shown in the following reaction schemes A and B wherein $R^2$, Y, and $R^6$ are defined above, unless otherwise indicated. As will be evident to those skilled in the art and as demonstrated in the examples, reactive groups such as amino, hydroxy, carboxy, etc. may be protected by standard methods and subsequently deprotected when it is appropriate.

REACTION SCHEME A
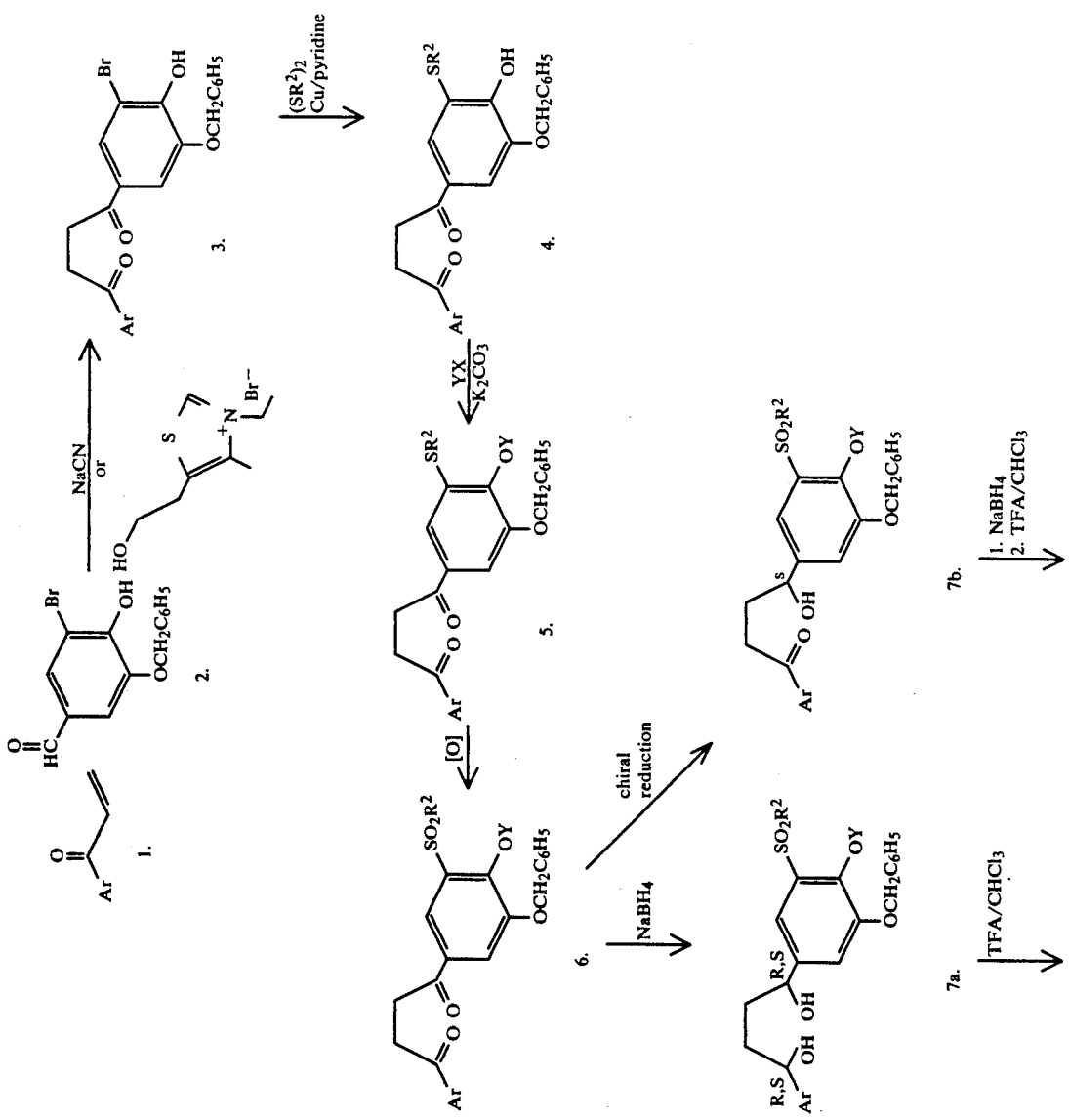

REACTION SCHEME A
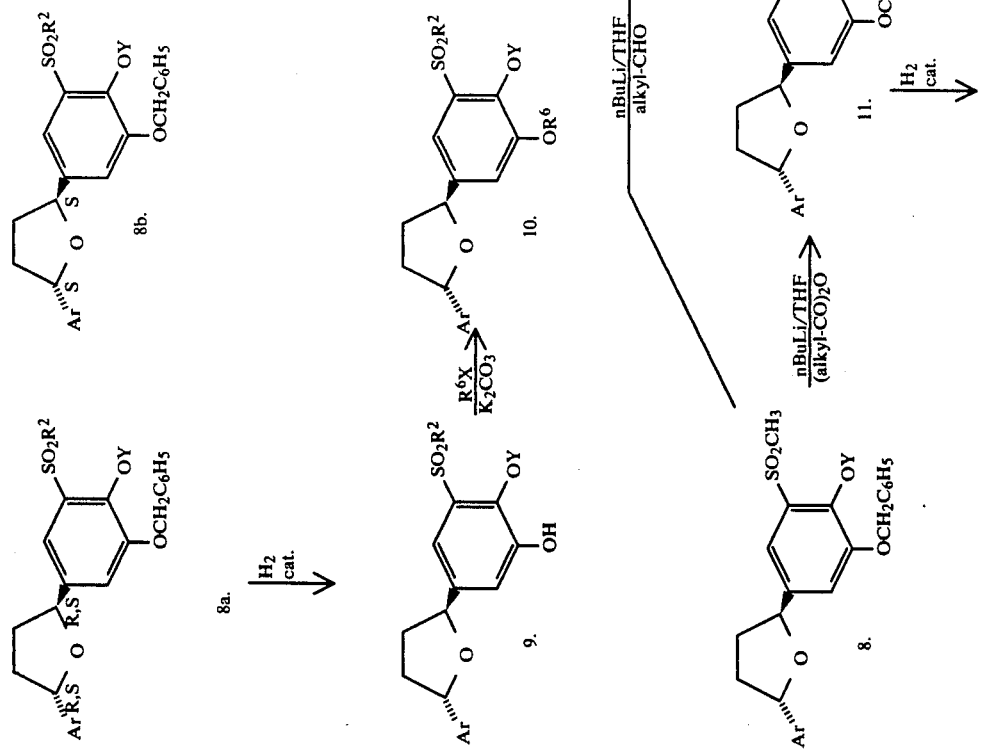

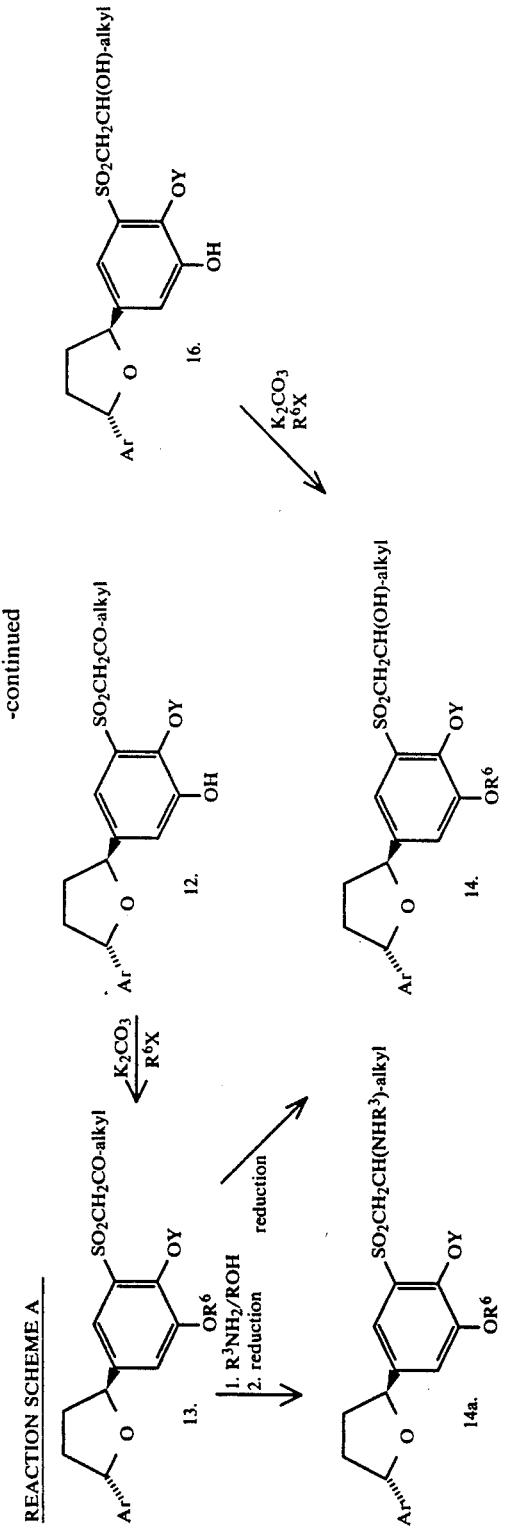

5,011,847
REACTION SCHEME A: ALTERNATE DIKETONE PREPARATION
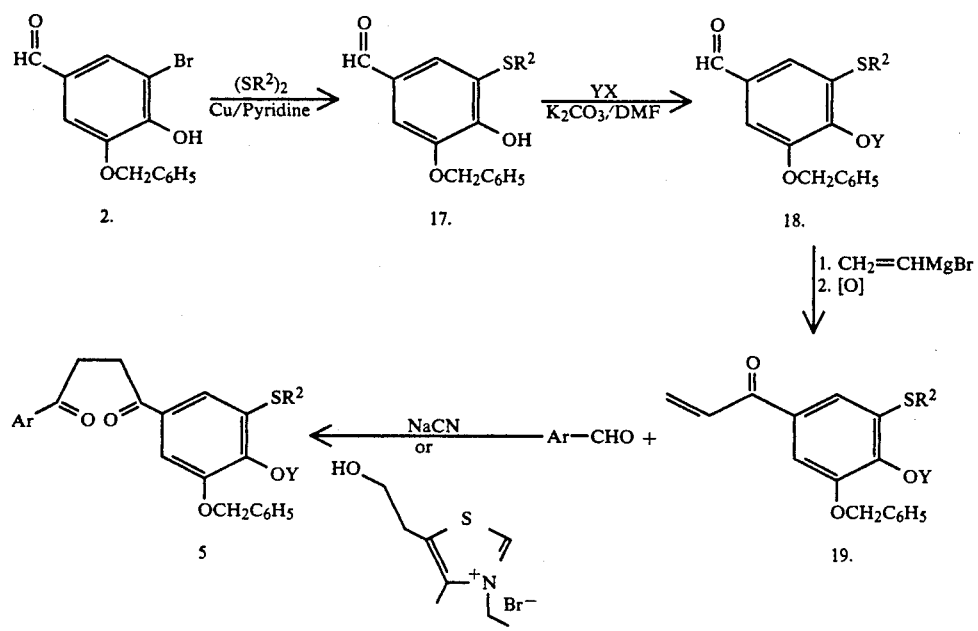
REACTION SCHEME B
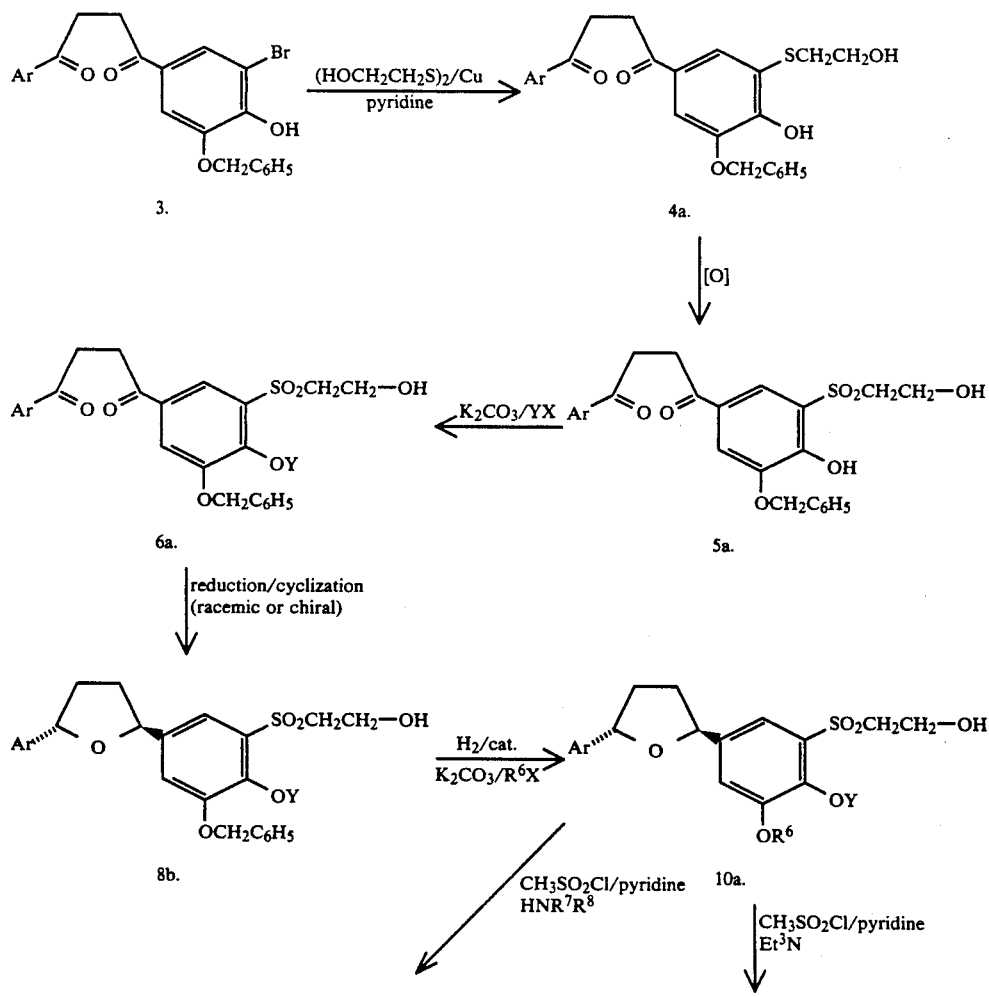

REACTION SCHEME B

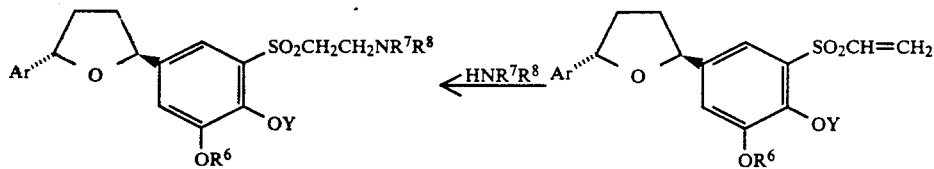

21.                             20.

Scheme A

The compounds of formula I may be prepared according to a sequence beginning with 5-benzyloxy-3-4-bromohydroxybenzaldehyde 1 which can be prepared according to the procedures outlined by J. Thiem [J. Chem. Soc. Perkin I, 1186–1190 (1977)]. One of several alternative approaches to preparing Diketone 3 is by reacting aldehyde 2 with vinylketone 1 and a base such as triethylamine with a catalytic amount of cyanide ion in DMF or 3-ethyl 5 (2-hydroxyethyl)-4-methylthiazolium bromide in DMF. Vinylketone 1 may be prepared from an arylmethylketone via conversion to a Mannich base, quaternization and elimination by standard procedures. Alternatively, the vinyl ketone may be prepared by addition of a vinyl nucleophile such as vinylmagnesium bromide to an arylaldehyde followed by oxidation of the alcohol to a ketone using a reagent such as manganese dioxide. Diketone is reacted with the appropriate disulfide $(SR^2)_2$, and copper powder in pyridine at elevated temperatures to provide compound 4. The 4 position may then be derivatized by alkylation with the appropriate alkylhalide, mesylate, or tosylate Y-X, using a base such as $K_2CO_3$ in a suitable solvent such as dimethylformamide (DMF) or tetrahydrofuran (THF) to provide compound 5. Alternatively, it is possible to prepare compound 5 by reversing the order of the last two steps. Oxidation of the sulfide group of compound 5 with an oxidizing agent such as m-chloroperoxybenzoic acid (mCPBA) in methylene chloride ($CH_2Cl_2$) provides sulfone 6. It is sometimes convenient to prepare diketone 5 via an alternate route beginning with preparation of arylvinylketone 19. This compound may be prepared by reacting aldehyde 2 with the appropriate disulfide $(SR_2)_2$, and copper powder in pyridine at elevated temperatures to provide compound 17. The 4-position may then be derivatized by alkylation with the appropriate alkylhalide, mesylate, or tosylate Y-X, using a base such as $K_2CO_3$ in a suitable solvent such as dimethylformamide (DMF) or tetrahydrofuran (THF) to provide compound 18. Alternatively, it is possible to prepare compound 18 by reversing the order of the last two steps. Aldehyde 18 may then be reacted with vinylmagnesium bromide followed by oxidation to give arylvinylketone 19 which is then converted to diketone 5 by procedures previously described.

Furan 8a is prepared via reduction of diketone 6 with reducing agents such as sodium borohydride ($NaBH_4$) in ethyl alcohol (EtOH) or a mixture of THF and methanol ($CH_3OH$) at elevated temperatures, or lithium aluminum hydride ($LiAlH_4$) in diethylether or THF at 0° C. Alternative methods include catalytic reduction using hydrogen and catalysts such as palladium, platinum, or rhodium. The resulting dialcohol 7a is dissolved in chloroform ($CHCl_3$) and carefully reacted with a dilute solution of trifluoroacetic acid (TFA) in $CHCl_3$ at 0° C. If adequate care is taken with this reaction the trans-furan 8a is produced as the major product and can be separated from the cis diastereomer by chromatography on silica gel normally eluting with a mixture of hexanes and ethyl acetate. Alternative methods of furan formation from 7a include such reagents as methanesulfonyl chloride-triethylamine or triphenylphosphine dibromide. The desired trans isomer 8a is usually a less polar material than the cis isomer on silica gel. The usually preferred chiral (S,S)-enantiomer may be prepared from diketone 6 by the specific reduction to ketoalcohol 7b using a bulky reducing agent such as lithiumtri-t-butoxyaluminumhydride [$LiAlH(OtBu)_3$], or controlled reduction with $NaBH_4$. Ketoalcohol 7b can be chemically resolved via the its 3-0-methylmandelate esters to provide chiral (S)-ketoalcohol 7b. Alternatively, compound 7b can be prepared in the chiral (S) form by using a chiral reducing agent such as the lithiumaluminumhydride (S) ( )-1,1'-bi-2-naphthol complex in THF normally at −78° C. chiral trans-furan 8b is prepared by sequential reduction of the remaining ketogroup with $NaBH_4$ and cyclization with TFA as for compound 8a. The 5'-position is then derivatized by removal of the benzyl protecting group by standard deprotection methods such as hydrogenation using a catalyst such as palladium on carbon in a solvent such as methanol (MeOH), ethanol (EtOH), or ethyl acetate. The free phenol may then be alkylated with the appropriate alkylating agent $R^6X$ where X is a halide, mesylate or tosylate and a base such as $K_2CO_3$ in DMF, EtOH or another suitable solvent.

A variant of Scheme A is the further elaboration of compound 8a or 8b where $R^2$ is methyl. This compound may be acylated with by reaction with n-butyllithium in THF at −78° C. followed by an ester, acid chloride or anhydride such as ethyl acetate, acetylchloride or acetic anhydride to give ketosulfone 11 which can be further elaborated into compound 13 by procedures previously outlined. A further elaboration is to reduce ketosulfone 13 to hydroxysulfone 14 using a reducing agent such as $NaBH_4$ in EtOH, or THF and $CH_3OH$. Alternatively, compound 11 can be similarly reduced to hydroxysulfone 15 which can then be deprotected and alkylated to give 14. Alternatively, hydroxysulfone 15 can be produced directly from compound 8 by reaction with the appropriate aldehyde after reacting 8a or 8b with nBu-tyllithium or a similar base.

Other elaborations at position 3' may be carried out starting with compound 8a or 8b ($R^2=CH_3$, Ethyl, etc.) by procedures analogous to those described herein.

A further series of amino compounds 14a can be prepared from ketosulfone 13 or 15 by reacting them hydroxylamine or substituted amines $R^3NH_2$ in an alcoholic solvent such as ethanol (ETOH) to obtain oximes or imines. These imines or oximes may then be reduced to free or substituted amines 14a employing reducing agents such as sodium borohydride, sodium cyanoborohydride in ETOH or by catalytic hydrogenation by methods previously described.

Scheme B

3'-(2-aminoethylsulfone) analogs (21)

A series of substituted or unsubstituted 2-aminoethylsulfone analogs 21 may be prepared by the scheme outlined in Process B. 2-hydroxyethylsulfone compounds 10a can be prepared by methods previously described and can then be derivatized as their tosylates or methanesulfonates by methods known to those in the art. Alternatively, the hydroxy group may be converted to a halide such as bromo, by one of a variety of commonly used methods such as triphenylphosphine and N-bromosuccinimide, or carbon tetrabromide or by phosphorus tribromide. Elimination to vinylsulfone 20 may be achieved by reacting the bromide, tosylate, or mesylate with a tertiary amine such as triethylamine. The vinyl sulfone 20 may then be reacted with an amine $R^7R^8NH$ in a solvent such as acetonitrile producing aminoethylsulfones 21. Compounds of structure 21 may also be prepared from the precursor mesylates, etc. by reacting them directly with amines $R^7R^8NH$.

This invention also relates to a method of treatment for patients (or mammalian animals raised in the dairy, meat, or fur industries or as pets) suffering from disorders or diseases which can be attributed to PAF as previously described, and more specifically, a method of treatment involving the administration of the PAF antagonists of formula (I) as the active constituents.

Accordingly, the compounds of formula (I) can be used among other things to reduce pain and inflammation, to correct respiratory, cardiovascular, and intravascular alterations or disorders, and to regulate the activation or coagulation of platelets, to correct hypotension during shock, the pathogenesis of immune complex deposition and smooth muscle contractions.

For the treatment of inflammation such as rheumatoid arthritis, osteoarthritis, and eye inflammation, cardio-vascular disorder, asthma, shock syndrome or other diseases mediated by the PAF, the compounds of formula (I) may be administered orally, topically. Parentally, by inhalation spray or rectally in dosage unit formulations containing conventional non toxic pharmaceutically acceptable carriers, adjuvants and vehicles. The term parental as used herein includes subcutaneous injections, intravenous, intramuscular, intrasternal injection or infusion techniques. In addition to the treatment of warm blooded animals such as mice, rats, horses, cattle, sheep, dogs, cats, etc., the compounds of the invention are effective in the treatment of humans.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in the U.S. Pat. Nos. 4,256,108; 4,166,452; and 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil.

Aqueous suspensions contain the active materials in admixture with excipients suitable for the manufacture of aqueous suspensions. Such excipients are suspending agents, for example sodium carboxymethylcellulose, methylcellulose, hydroxypropylmethylcellulose, sodium alginate, polyvinylpyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxy- cetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents. The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parentally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic monoor diglycerides. In addition, fatty acids such as oleic acid find use in the preparation of injectables.

The compounds of formula (I) may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, jellies, solutions or suspensions, etc., containing the compounds of Formula (I) are employed.

Dosage levels of the order of from about 0.05 mg to about 140 mg per kilogram of body weight per day are useful in the treatment of the above-indicated conditions (about 2.5 mg to about 7 gms. per patient per day). For example, inflammation may be effectively treated by the administration of from about 0.01 to 50 mg of the compound per kilogram of body weight per day (about 1.0 mg to about 3.5 gms per patient per day).

The amount of active ingredient that may be combined with the carrier materials to produce a single dosage form will vary depending upon the host treated and the particular mode of administration. For example, a formulation intended for the oral administration of humans may contain from 0.5 mg to 5 gm of active agent compounded with an appropriate and convenient amount of carrier material which may vary from about 5 to about 95 percent of the total composition. Dosage unit forms will generally contain between from about 1 mg to about 500 mg of an active ingredient.

It will be understood, however, that the specific dose level for any particular patient will depend upon a variety of factors including the activity of the specific compound employed, the age, body weight, general health, sex, diet, time of administration, route of administration, rate of excretion, drug combination and the severity of the particular disease undergoing therapy.

A representative number of compounds of the instant invention of the formula (I) exhibit in vitro antagonistic activities with respect to PAF:

The compounds of formula (I) inhibit PAF-induced functions in both the cellular and tissue levels by changing the PAF binding to its specific receptor site. The ability of a compound of formula (I) to inhibit the PAF binding to its specific receptor binding site on rabbit or human platelet or PMN plasma membranes was measured by a recently developed assay.

The inhibition of $^3[H]$-PAF or $^3[H]$-N-methylcarbamoyl-PAF binding to the human or rabbit platelet or PMN plasma membrane by a PAF antagonist of formula (I) was determined by a method employing isotopic labeling and filtration techniques. Generally, a series of Tris-buffered solutions of the selected antagonist at predetermined concentrations were prepared. Each of these solutions contains 1 pmole of $^3H$-PAF, a known amount of the test antagonist, and a sufficient amount of the pH 7.5 Tris-buffer solution (10 mM Tris, 0.25% bovine serum albumin, and 150 mM NaCl per ml water) to make the final volume of 1 ml. After adding into a set of test tubes each with 100 $\mu$g of the platelet plasma membrane suspension (S. B. Hwang, et al., *Biochemistry*. Vol. 22, pp. 4756–4763, 1983) and one of the Tris-buffer solutions described above, the resulting mixture in each test tube was incubated at 0° C. for about one hour or until the reaction was complete. Two control samples, one of which ($C_1$) contains all the ingredients described above except the antagonist and the other ($C_2$) contains $C_1$ plus a 1000-fold excess of unlabeled PAF, were also prepared and incubated simultaneously with the test samples. After the incubation was completed, the contents of each test tube were filtered under vacuo through a Whatman GF/C fiberglass filter and the residue washed rapidly several times with a total of 20 ml cold (0°–5° C.) Tris buffer solution. Each washed residue was then suspended in 10 ml scintillation solution (Aquasol 2, New England Nuclear, Conn.) and the radioactivity was counted in a Packard Tri-Carb 460CD Liquid Scintillation System. Defining the counts from a test sample as "Total binding with antagonist"; the counts from the control sample $C_1$, as "Total binding $C_1$"; and the counts from the control sample $C_2$ as "non-specific binding $C_2$", the percent inhibition of each test antagonist can be determined by the following equations:

$$\% \text{ Inhibition} = \frac{(\text{Total binding } C_1) - \text{Total binding with antagonist}}{\text{Specific binding}} \times 100$$

Specific binding = (Total binding $C_1$)-(non-specific binding $C_2$)

The tested compounds of formula (I) inhibit in vitro PAF-induced platelet aggregation (rabbit or human platelets); PAF induced guinea pig peritoneal PMN (polymorphonuclear leukocytes) aggregation., PAF-induced human PMN secretion; and PAF-induced guinea pig smooth muscle contraction although they are not $H_2$-receptor antagonists. They are also shown in these inhibition studies to be highly specific to PAF. For example, they do not inhibit the binding of $H_1$ antagonist ($^3H$-pyrilamine) to guinea pig brain membrane, nor do they inhibit the binding of a cholecystokinin (CCK) receptor based on an assay on isolated rat pancreas membrane. Furthermore, they affect no or only minute inhibition on the histamine-induced ileum contraction from guinea pigs.

The antagonistic activity of representative compounds of structural formula (I) in the trans configuration is summarized in the following table.

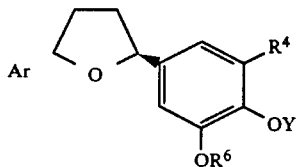

| R4 | Y | R6 | | % Inhibition* |
|---|---|---|---|---|

Ar = (3-pyridyl)

| R4 | Y | R6 | | % Inhibition* |
|---|---|---|---|---|
| SO₂C₃H₇ | CH₂CH₂CH₃ | CH₂COCH₃ | 30 nM | 66% |
|  |  |  | 3 nM | 12% |

Ar = 2,3-dimethoxypyridyl (CH₃O, CH₃O substituents)

| R4 | Y | R6 | | % Inhibition* |
|---|---|---|---|---|
| SO₂C₃H₇ | CH₂CH₂CH₃ | CH₂COCH₃ | 30 nM | 93% |
|  |  |  | 3 nM | 63% |
| SO₂C₃H₇ | CH₂CH₂CH₃ | CH₂CH(OH)CH₃ | 30 nM | 100% |
|  |  |  | 3 nM | 54% |
| SO₂CH₂CH₂CH₂OH | CH₂CH₂CH₃ | CH₂COCH₃ | 30 nM | 66% |
|  |  |  | 3 nM | 30% |
| SO₂CH₂CH₂CH₂OH | CH₂CH₂CH₃ | CH₂CH(OH)CH₃ |  |  |
| SO₂CH₂CH(OH)CH₃ | CH₂CH₂CH₃ | CH₂COCH₃ | 30 nM | 81% |
|  |  |  | 3 nM | 31% |
| SO₂CH₂CH(OH)CH₃ | CH₂CH₂CH₃ | CH₂CH(OH)CH₃ | 30 nM |  |
| SO₂CH₂CH(OH)CH₃ | CH₂CH₂CH₃ | CH₂CH₂CH₂OH | 30 nM | 75% |
|  |  |  | 3 nM | 16% |
| SO₂CH₂CH(OH)CH₃ | CH₂CH₂CH₃ | CH₂CH₂OH | 30 nM | 58% |
|  |  |  | 3 nM | 13% |
| SO₂CH₂COCH₃ | CH₂CH₂CH₃ | CH₂CH₂CH₂OH | 30 nM | 87% |
|  |  |  | 3 nM | 43% |

Ar = 2,3-dimethoxy-pyrazinyl (CH₃O, CH₃O, N, N)

| R4 | Y | R6 | | % Inhibition* |
|---|---|---|---|---|
| SO₂CH₂CH₂CH₃ | CH₂CH₂CH₃ | CH₂COCH₃ | 30 nM | 100% |
|  |  |  | 3 nM | 58% |
| SO₂CH₂CH₂CH₃ | CH₂CH₂CH₃ | CH₂CH(OH)CH₃ | 30 nM | 100% |
|  |  |  | 3 nM | 60% |
| SO₂CH₂CH(OH)CH₃ | CH₂CH₂CH₃ | CH₂COCH₃ | 30 nM | 81% |
|  |  |  | 3 nM | 42% |

*Inibition of the binding of [³H] N-methylcarbamoyl-PAF to human platelet membranes.

The following examples illustrate the preparation of representative compounds of this invention and pharmaceutical compositions thereof and as such are not to be considered as limiting the invention set forth in the claims appended hereto.

EXAMPLE 1 trans-2-[3-n-Propylsulfonyl-4-n-propoxy-5-(2-oxopropoxy) phenyl -5 [5 (2.3 dimethoxy)pyridyl]tetrahydrofuran

STEP 1A: 3-Methylthio-4-hydroxy-5-benzyloxybenzaldehyde

A five liter flask equipped with a mechanical stirrer was charged with 100 g of 3-bromo-4-hydroxy-5-benzyloxybenzaldehyde, 80 g Cu powder, 80 mL methyldisulfide and 1.7L pyridine, and the mixture was heated at 90° C. overnight with gentle stirring. The following day, the reaction mixture was filtered and most of the pyridine (1.3L) was distilled off. The remaining solid residue was washed with about 2L of methylene chloride and combined with the residue left after pyridine evaporation. The combined organic fraction was washed with 1.5N HCl until the dark methylene chloride layer turned light brown and the aqueous layer was clear. The resulting light brown methylene chloride layer was dried over MgSO₄ and filtered through a bed of silica gel. Evaporation and crystallization from methylene chloride-hexane gave the title compound: NMR(200 MHz, CDCl₃) δ 2.50(s, SCH₃), 5.20(s, OCH₂Ar), 6.72(s, OH), 7.34–7.46(m, ArH), 9.78(s, ArCHO).

STEP 1B:
3-Methylthio4-n-propoxy-5-benzyloxybenzaldehyde 64.5 g of 3-Methylthio-4-hydroxy-5benzyloxybenzaldehyde dissolved in a 75 mL of DMF was treated with 50 g of K₂CO₃ and 32 g of 1-bromopropane and stirred overnight at 70°. The next day about 1.5 liters of methylene chloride and an equal amount of water was added to the reaction mixture. The organic layer was removed, washed three times with distilled water, dried over MgSO₄ and evaporated to a viscous liquid that solidified slowly: NMR(200 MHz, CDCl₃) δ 1.02 (t, CH₂CH₂CH₃), 1.82(m, CH₂CH₂CH₃), 2.48(s, SCH₃), 4.12(t, OCH₂CH₂CH₃), 5.18(s, OCH₂Ar), 7.26–7.52(m, ArH), 9.86(s, ArCHO).

STEP 1C: 5-(2.3-dimethoxy)pyridylvinylketone

To 100 ml of vinylmagnesium bromide (1.0M in THF) at 0° C. was added dropwise 15.2 gm of 2,3 dimethoxypyridyl 5-carboxaldehyde dissolved in 100 ml of THF. After stirring 0.75 hours at room temperature, to the reaction mixture was carefully added 7 gm of NH₄Cl, 100 ml of H₂O and 100 ml of methylene chloride. The organic fractions were dried over MgSO₄, filtered through a thin layer of silica gel and evaporated in vacuo. The vinyl alcohol was then dissolved in 100 ml of methylene chloride and 100 ml of hexanes and to this solution waS added 15 gm of MnO₂ and the reaction was stirred at room temperature until reaction was completed. The crude reaction mixture was purified by chromatography through a short column of silica gel MeCl₂/Hexane 50:50 to provide the title compound. NMR (200 MHz, CDCl₃) δ 3.95 & 4.10 (2s, 2OCH₃), 5.94 (d, COCH=CH₂), 6.46 (d, COCH=CH₂), 7.14 (dd, COCH=CH2), 7.65 & 8.38 (d, ArH).

STEP 1D:
1-(3-methylthio-4-propoxy-5-benzyloxyphenyl -4-[5-(2,3-dimethoxy)-pyridyl]butan-1.4-dione 11 g 3-methylthio-4-n-propoxy-5-benzyloxybenzaldehyde, 6.8 g of 5 (2,3-dimethoxy)pyridylvinylketone, 3g of 3 ethyl 5-(2 hydroxyethyl) 4 methylthiazolium bromide, 5 mL of triethyl amine dissolved in 50 ml of dimethylformamide was heated at 60° C. overnight, and the reaction mixture was treated with 100 mL of 1.5N HCl and the aqueous layer decanted. The residue was treated again with fresh 100 mL of 1.5N HCl and decanted two more times. The remaining residue was crystallized from 400 mL of methanol and washed thoroughly with methanol, hexane, and methanol and dried to the title compound as a crystalline solid: TLC: Rf=0.9 (40:60 Hexanes:Ethyl Acetate); NMR (200 MHz, CDCl₃) δ 1.04 (t, OCH₂Ch₂CH₃), 1.82 (m, OCH₂CH₂CH₃), 2.48 (s, SCH₃), 3.42 (s, CO-CH₂-CH₂-CO), 3.94 & 4.12 (2s, 2OCH₃) 4.11 (t, OCH₂CH₂CH₃) 5.18 (s, O-CH₂-Ph) 7.30–7.50 (m, OCH₂Ph+1-ArHs) 7.63 and 8.52 (dd, 4.Pyr Hs).

STEP 1E:
1-(3-Methylsulfonyl-4-n-propoxy-5-benzyloxyphenyl) -4-[5-(2,3-dimethoxy)-pyridyl]butan 1 4-dione 8.45 g of 1 (3-methylthio-4 propoxy-5-benzyloxyphenyl) -4-[5-(2,3-dimethoxy)-pyridyl]butan-1, 4-dione dissolved in 100 mL of methylene chloride was cooled in ice bath and treated with 6 g of mCPBA (80%) in small portions. After 2–3 h of stirring, the mixture was cooled to 0° C., filtered to remove 3-chlorobenzoic acid and evaporated to a small volume. The residue obtained as such was taken up in ethyl acetate, washed with aqueous NaOH, water, brine, dried over MgSO₄ and evaporated. The residue was crystallized from methanol to yield the title compound:TLC, silica gel(4:6, hexanes: ethylacetate) Rf=0.59; NMR (200 MHz, CDCl₃) δ 0.99 (t, OCH₂CH₂CH₃), 1.86 (m, OCH₂CH₂CH₃), 3.30 (s, SO₂CH₃), 3.52 (s, CO-CH₂-CH₂-CO), 3.92 & 4.12 (2s, 2OCH₂ 4.28 (t, OCH₂CH₂CH₃), 5.20 (s, O-CH₂-Ph), 7.42 (m, OCH₂Ph), 7.62 & 8.52 (dd, 4 Pyr Hs), 7.94 & 8.27 (dd, 1 ArH).

STEP 1F:
1-(3-Methylsulfonyl-4-n-propoxy-5-benzyloxyphenyl) -4-[5-(2,3-dimethoxy)-pyridyl]butan-1,4-diol 8.7 g of 1 (3 methylsulfonyl 4 n propoxy-5-benzyloxyphenyl) -4-[5-(2,3-dimethoxy) pyridyl]butan-1, 4-dione (STEP E) dissolved in a mixture of 80 mL dry THF and 200 mL of methanol was treated with 0.9 g of NaBH₄ (added portionwise) at 0° C. and stirred for 3 h. The reaction mixture was then allowed to gradually warm to room temperature and stirring was continued for additional 2 h. After the completion of the reaction,(tlc, silica, 4:6, hexanes: ethylacetate) the solvent was evaporated at reduced pressure and the residue obtained as such was redissolved in 300 ml of ethyl acetate. The organic layer was washed with 1.5N HCl, distilled water and brine respectively, and then dried over MgSO₄ and evaporated to a colorless syrup which was used without further purification.

STEP 1G:
trans-2-(3-Methylsulfonyl-4-n-propoxy-5-benzyloxyphenyl) -5-[5-(2,3-dimethoxy)pyridyl]tetrahydrofuran 1-(3-methylsulfonyl-4-n-propoxy-5-benzyloxyphenyl) -4-[5-(2,3 dimethoxy)-pyridyl]butan-1, 4-diol (prepared in STEP 1F) dissolved in 100 mL of chloroform was treated dropwise with 10 ml of Trifluoroacetic acid and stirred for 16 h at 0° C. The reaction mixture was washed with 5% NaOH, water, brine, dried over MgSO₄ and evaporated to a crystalline salt. The trans isomer of the title compound was crystallized from ether: NMR (200 MHz, CDCl₃) δ 1.00 (t, OCH₂CH₂CH₃), 1.85 (m, OCH₂CH₂CH₃) 2.00 & 2.49 (m, 3Hs & 4Hs), 3.28 (s, SO₂CH₃), 3.93 & 4.04 (2s, 2OCH₃) 4.19 (t, OCH₂CH₂CH₃), 5.20 (s, OCH₂Ar), 5.20 (m, 2H & 5H), 7.14 & 7.73 (dd, 5 Pyr Hs), 7.36 & 7.54 (dd, Z-ArHs), 7.42 (m, Ph).

STEP 1H: trans-2-(3-n propylsulfonyl-4-n-propoxy-5-benzyloxyphenyl) -5-[5-(2,3-dimethoxy)pyridyl]tetrahydrofuran To a solution of 1 gm of trans-2-(3-methylsulfonyl-4-propoxy-5-benzyloxyphenyl) -5-[5-(2,3-dimethoxy)-pyridyl]tetrahydrofuran in 7 ml of THF at −78° C. was added 1.3 ml of n butyllithium (1.3M solution in hexanes). After stirring for 20 min., 0.2 mL of iodoethane was added to the reaction mixture. After stirring a further 30 min., NH4Cl, H2O and ether were added to the reaction mixture. The combined organic fractions were dried over MgSO4, evaporated to dryness and chromatographed on silica gel eluting with ethyl acetate/hexane 2:3 to provide the title compound. NMR (200 MHz, CDCl3) δ 1.02 (dt, OCH2CH2CH3+SO2CH2CH2CH3), 1.66-1.92 (m, OCH2CH2CH3+SO2CH2CH2CH3), 2.00+2.49 (2 m, 3 Hs+4 Hs), 3.41 (t, SO2CH2CH2CH3), 3.94 & 4.04 (2s, 2OCH3), 4.18 (t, OCH2CH2CH3) 5.20 (s, OCH2Ph), 5.20 (m, 2H & 5H), 7.14 & 7.74 (dd, 5 Pyr Hs, 7.36 & 7.52 (2d, 2 ArHs) 7.43 (m, Ph).

STEP 1I:
trans-2-(3-n-Propylsulfonyl-4-n-propoxy-5-hydroxyphenyl) -5-[5-(2,3-dimethoxy)pyridyl]tetrahydrofuran A solution of 0.55 gm of trans 2 (3-n propylsulfonyl-4-n-propoxy-5-benzyloxyphenyl) -5-[5-(2,3-dimethoxy) pyridyl]tetrahydrofuran in 60 ml of ethylacetate and 0.1 gm of Pd/C (10%) was hydrogenated at 40 psi for 2.5 hours. The resulting reaction mixture was filtered through a thin pad of celite and evaporated in vacuo to obtain the title compound. NMR (200 MHz, CDCl3) δ 1.00 (t, SO2CH2CH2CH3), 1.09 (t, OCH2CH2CH3), 1.72 (m, SO2CH2CH2CH3), 1.91 (m, OCH2CH2CH3), 2.00 +2.49 (2m, 3Hs +4Hs) 3.34 (t, SO2CH2CH2CH3), 3.92 +4.03 (2s, S OCH3), 4.13 (t, OCH2CH2CH3), 5.22 (t, 2H+5H) 5.65 (m, OH), 7.14 +7.73 (2d, 5-Pyr Hs), 7.33+7.48 (2d, Z-ArHs).

STEP 1J:
trans-2-(3-n-propylsulfonyl-4-n-propoxy-5-(2-bromoethoxy) phenyl)-5-[5-(2,3-dimethoxy)pyridyl]tetrahydrofuran To a solution of 0.5 gm of trans-2 (3 n propylsulfonyl-4-n-propoxy-5-hydroxyphenyl) -5-[5 (Z,3 dimethoxy) pyridyl]tetrahydrofuran in 20 ml of acetone was added 3 ml of 1,2-dibromoethane and 1.5 gm of finely ground K2CO3 and the reaction mixture was allowed to stir overnight at 55° C. The reaction mixture was then diluted with methylene chloride (50 ml) filtered and thoroughly evaporated in vacuo to give the title compound which was used without further purification. NMR (200MHZ, CDCl3) δ 1.00 (t, SO2CH2CH2CH3), 1.07 (t, OCH2CH2CH3), 1.72 (m, SO2CH2CH2CH3), 1.90 (m, OCH2CH2CH3), 2.02+2.50 (2m, 3Hs+4Hs), 3.40 (t, SO2CH2CH2CH3), 3.72 (t, OCH2CH2Br) 3.91+4.03 (2s, S OCH3) 4.20 (t, OCH2CH2CH3), 4.41 (t, OCH2CH2Br), 5.22 (m, 2H+5H) 7.12+7.73 (2d, 5 Pyr Hs), 7.25+7.53 (2d, Z ArHs).

STEP 1K:
trans-2-[3-n-propylsulfonyl-4-n-propoxy-5-(2-oxopropoxy)phenyl]-5-[5-(2.3-dimethoxy)pyridyl]tetrahydrofuran This compound was prepared by using the procedure described in 1J and replacing 1,2-dibromoethane with chloroacetone. Characteristic NMR (200 MHz, CDCl3) δ 2.34 (s, CH3C=0).

EXAMPLE 2
trans-2-[3-n-propylsulfonyl-4-n-propoxy-5-(2-hydroxypropoxy)phenyl]-5-[5-(2,3-dimethoxy)pyridyl]tetrahydrofuran The title compound was prepared from the title compound of example 1 by reduction with NaBH4 in ethanol, stirring at room temperature. The title compound was purified by passing it through a twin pad of silica gel eluting with ethyl acetate. Characteristic NMR (200 MHz, CDCl3) δ 1.34 (d, CH3 CHOH)

EXAMPLE 3
trans-2-[3-(2-Hydroxypropyl)sulfonyl-4-n-propoxy 5 (3 hydroxypropoxy)phenyl]5-8 5-(2,3-dimethoxy)pyridyl]tetrahydrofuran

STEP 3A:
trans-2-(3-(2-Hydroxypropyl)sulfonyl-4-n-propoxy-5-benzyloxyphenyl) -5-[5-(2,3-dimethoxy) pyridyl]tetrahydrofuran The title compound was prepared from trans-2-(3 methylsulfonyl-4-n propoxy-5-benzyloxyphenyl)-5-[5-(2,3-dimethoxy) pyridyl]tetrahydrofuran according to procedures described in Example 1, Step H using acetaldehyde in place of iodoethane. NMR (200 MHz, CDCl3) δ 0.98 (t, OCH2CH2CH3), 1.26 (d, SO2CH2CHOHCH3), 1.85 (m, OCH2CH2CH3), 2.00+2.49 (2 m, 3 Hs+ 4 Hs), 3.40-3.66 (m, SO2CH2CHOHCH3) 3.94+4.04 (2s, 2OCH3), 4.20 (m, OCH2CH2CH3+SO2CH2CHOHCH3), 5.20 (s, OCH2Ar) 5.20 (m, 2-CH+5-CH), 7.14+7.74 (2d, 5-Pyr Hs) 7.34-7.56 (m, 2-ArHs+Ph).

STEP 3B:
trans-2-(3-(2-hydroxypropyl)sulfonyl-4-n-propoxy-5hydroxyphenyl) -5-[5-(2,3-dimethoxy) pyridyl]tetrahydrofuran The title compound was prepared according to procedures described in Example 1, Step I. NMR (200 MHz, CDCl3) δ 1.08 (t, OCH2CH2CH3), 1.26 (d, SO2CH2CHOHCH3), 1.90 (m, OCH2CH2CH3), 2.00+2.50 (2m, 3-CH2+4CH2), 3.36-3.60 (m, SO2CH2CHOHCH 3.92+4.04 (2s, 2OCH3), 4.06-4.36 (m, OCH2CH2CH3+SO2CH2CHOHCH3), 5.22 (t, 2-CH+5-CH) 6.08 (m, OH), 7.14+7.74 (2d, 5-Pyr Hs) 7.34+7.50 (2dd, 2-Ar Hs).

STEP 3C:
trans-2-[3-(2-Hydroxypropyl)sulfonyl-4-n-propoxy-5-(3-hydroxypropoxy)phenyl]-5[5-(2,3-dimethoxy)-pyridyl]tetrahydrofuran To a solution of 400 mg trans-2-[3-(2-hydroxypropyl)sulfonyl-4-n-propoxy-5-hydroxyphenyl]-5-[5-(2,3-dimethoxy) pyridyl]tetrahydrofuran in 5 ml of acetone and 0.5 ml of bromo-n-propanol was added [400 mg]of K2CO3and the reaction mixture was heated overnight at 55° C. NMR (200 MHz CDCl3) δ 1.07 (t, OC2CH2CH3), 1.27 (d, SO2CH2CHOHCH3) 1.90 (m, OCH2CH2), 1.98−2.22+2.52 (2 m, 3-CH2+ 4 CH2; OCH2CH2CH2OH), 3.40-3.66 (m, SO2CH2CHOH), 3.80-3.92 (m, OCH2CH2CH2OH), 3.93+4.04 (2s, 2 OCH3), 4.12-4.34 (m, OCH2CH2CH3SO12CH2CHOHCH3), 4.26 (t, OCH2CH2CH2OH), 5.25 (t, 2-CH - 5-OH), 7.14+7.76 (2d, 5 Pyr Hs), 7.34+7.52 (2 dd, 2-ArHs).

EXAMPLE 4
trans-2-[3-(2-Hydroxypropyl)sulfonyl-4-n-propoxy 5-(2-hydroxyethoxy)phenyl]-5-[5-(2,3-dimethoxy)-pyridyl]tetrahydrofuran The title compound was prepared according to procedures described in Example 3. NMR (200 MH , CDCl3) δ 1.06 (t, CH3CH2CH2O),, 1.24 (d, CH3CHOH), 3.92 and 4.04 (3s, OCH3), 5.20 (m, 2-CH and 5-CH), 7.1–7.7 (m, Ar-H).

EXAMPLE 5 trans-2-[3-(2-Hydroxypropyl)sulfonyl-4-n-propoxy-5-(2-oxopropoxy)phenyl]-5-[5-(2,3-dimethoxy)pyridyl]tetrahydrofuran The title compound was prepared according to procedures outlined in Example 3. NMR (200 MHz, CDCl$_3$) δ 2.34 (S, CH$_3$C=0) 4.68 (s, CH$_3$COCH$_2$).

EXAMPLE 6 trans-2-[3-(2-Hydroxypropyl)sulfonyl 4-n-propoxy-5 (2 hydroxypropoxy)phenyl]-5-[5-(2,3-dimethoxy)pyridyl]tetrahydrofuran The title compound was prepared according to procedures described in Example 2. NMR (200 MHz, CDCl$_3$) δ 1.06 (t, CH$_3$CH$_2$CH$_2$) 1.27 (d, SO$_2$CH$_2$CHOHCH$_3$), 1.35 (d, CH$_3$CHOH), 3.92 and 4.03 (2s, 2OCH$_3$), 5.23 (m, 2-CH and 5-CH), 7.12–7.74 (Ar-H).

EXAMPLE 7 trans-2-[3-(2-Hydroxypropyl)sulfonyl-4-n-propoxy 5 (2 bromoethoxy) phenyl]-5-[5-(2,3-dimethoxy)pyridyl]tetrahydrofuran The title compound was prepared according to procedures described in Example 1, Step J. 1.06 (t, CH$_3$CH$_2$CH$_2$), 3.72 (t, BrCH$_2$CH$_2$), 4.02+4.03 (2s, 2OCH$_3$), 5.23 (m, 2-CH and 5-CH), 7.1–7.72 (Ar-H).

EXAMPLE 8 trans-2-[3-(2-oxopropyl)sulfonyl-4-n-propoxy-5-(3-hydroxypropoxy) phenyl]-5[5-(2,3-dimethoxy)pyridyl]tetrahydrofuran

STEP 8A: trans-2-(3-(2-Oxopropyl)sulfonyl 4-n-propoxy-5-benzyloxyphenyl) -5-[5-(2,3-dimethoxy)pyridyl]tetrahydrofuran The title compound was prepared from trans 2 (3 methylsulfonyl-4-n-propoxy-5-benzyloxyphenyl) -5-[5-(2,3-dimethoxy)pyridyl]tetrahydrofuran according to procedures described in Example 1, Step H using acetic anhydride in place of iodoethane. NMR (200 MHz, CDCl$_3$) δ 0.99 (t, CH$_3$CH$_2$CH$_2$), 2.36 (s, CH$_3$C=0), 3.92 +4.02 (2s, 2OCH$_3$), 4.48 (s, CH$_3$COCH$_2$), 7.1 7.7 (m, Ar-H).

STEP 8B: trans-2-[3-(2-Oxopropyl)sulfonyl 4-n-propoxy-5-(3-hydroxypropoxy) phenyl]-5-[5-(2.3-dimethoxy)pyridyl]tetrahydrofuran The title compound was prepared according to procedures outlined in Example 3. NMR (200 MHz, CDCl$_3$) δ 1.06 (t, CH$_3$CH$_2$CH$_2$), 2.39 (s, CH$_3$CO), 3.93 and 4.03 (2s, 2OCH$_3$), 4.16 and 4.23 (ea t, OCH$_2$CH$_2$), 4.28 (s, CH$_3$COCH$_2$), 5.20 (m, 2CH+5-CH), 7.1–7.72 (Ar-H).

EXAMPLE 9 trans-2-3-n-propylsulfonyl-4-n-propoxy-5-(2-oxopropoxy)phenyl]-5-(3-pyridyl)tetrahydrofuran The title compound was prepared according to procedures outlined in Example 1 beginning with the preparation of 3-pyridylvinylketone. NMR (200 MHz, CDCl$_3$) δ 1.05 (t, OCH$_2$CH$_2$CH$_3$) 1.24 (d, SO$_2$CH$_2$CHOHCH$_3$), 1.90 (m, OCH$_2$CH$_2$) 2.00+2.50 (m, 3-CH$_2$+4-CH$_2$), 3.40–3.64 (m, SO$_2$CH$_2$CHOHCH$_3$) 3.72 (t, OCH$_2$CH$_2$Pr) 3.91+4.02 (2s, 2OCH$_3$) 4.08–4.34 (m, OCH$_2$CH$_2$CH$_3$+SO$_2$CH$_2$CHOHCH$_3$) 4.41 (t, OCH$_2$CH$_2$BR) 5.22 (m, 2-CH - 5-CH) 7.12 +7.72 (2d, S Pyr Hs) 7.26+7.53 (2dd, 2-ArHs).

EXAMPLE 10 trans-2-[3-n-propylsulfonyl-4-n-propoxy-5-(2-oxopropoxy) phenyl]-5-[6-(2,3-dimethoxy)pyrazyl]tetrahydrofuran

STEP 10A: trans- 2,3-dimethoxypyrazine

A solution of 22 ml of sodium methoxide in methanol (25% w/w) was added to a stirred solution of 2,3-dichloropyrazine (6.3 gm, 0.04 mol) under N$_2$ at 25° C. After stirring for 16 hours an additional 3 ml of sodium methoxide was added with stirring for an added 5 hours. The reaction mixture was diluted with methylene chloride, filtered and the filtrate was evaporated in vacuo. The residue was dissolved in methylene chloride, washed with water, dried over MgSO$_4$, filtered and evaporated to give the title compound as a crystalline solid. NMR (CDCl$_3$) δ 4.01(s, 6H, —OCH$_3$), 7.60(s, 2H, ArH).

STEP 10B: 2-bromo-5,6-dimethoxypyrazine

A solution of 14.6 gm of N-bromosuccinamide, 32 ml of dry DMF was added to a stirred solution of 11 gm (0.078 mol) of 2,3 dimethoxypyrazine in 14 ml of DMF at 0° C. whereupon the reaction was warmed to 25° C. and stirred for 16 hours. The reaction mixture was then cooled in an ice bath and to it was added aqueous Na$_2$SO$_3$ to remove the bromine and this was poured into ice water. The resulting crystalline solid was filtered, triturated with water and dried to give the title compound. NMR (CDCl$_3$) δ 4.0, 4.02(2s, 6H, —OCH$_3$), 7.70(s,1H).

STEP 10C: 2,3-dimethoxy-5-formylpyrazine

To a stirred solution of 4.85 gm of 2-bromo-5,6-dimethoxypyrazine in 80 ml of dry ether under N$_2$ at −35° C. was added dropwise 14.5 ml of n butyllithium (1.6N in hexanes). After stirring for 0.5 hours at −35° C. 5.74 ml of dry DMF was added dropwise to the reaction mixture. This dark brown homogeneous solution was stirred at −20° C. for 1 hour and at 25° C. for 0.5 hours, then was quenched with an aqueous solution of NH$_4$Cl. The reaction mixture was extracted with methylene chloride, and the organic fractions were washed with water, brine and dried over MgSO4, and filtered and evaporated to give a red oil. Chromatography on a short silica gel column provided the title aldehyde and its hydrate which was used without further purification.

STEP 10D: 1-(3-methylthio-4-propoxy-5-benzyloxyphenyl) -4-[6-(2,3-dimethoxy) pyrazyl]butan 1.4 dione 1.76 gm of the title compound was prepared from 2,3-dimethoxy-5-formylpyrazine and 3-methylthio-4-propoxy-5-benzyloxyphenylvinylketone (prepared from 3-methylthio- 4-n-propoxy-5-benzyloxybenzaldehyde according to procedures in Example 1, Step C) according to procedures described in Example 1, Step D. Pertinent NMR signals: 2.48 (s,3H, SCH$_3$), 3.4,3.55(2m, 4H,C-3,C-4H).

STEP 10E:
trans-2-(3-n-propylsulfonyl-4-n-propoxy-5-benzyloxyphenyl) -5-[6-(2,3-dimethoxy)-pyrazyl]-tetrahydrofuran The title compound was prepared from 1-(3-methylthio-4-propoxy-5-benzyloxyphenyl) -4-[6-(2,3-dimethoxy)-pyrazyl]butan-1,4-dione according to procedures described in Example 1, Steps E-H. NMR (CDCl$_3$) δ 1.0(2t, 6H, CH$_2$CH$_3$), 1.6-2.6(m, CH$_2$CH$_2$CH$_3$, C-3H,C-4H), 3.38(m,2H, SO$_2$CH$_2$CH$_2$CH$_3$), 4.0, 4.1(2s,6H,OCH$_3$), 4.15(t 2H ,OCH$_2$CH$_2$CH$_3$), 5.1-5.3(m,4H,OCH$_2$Ar, C-2H,C-5H), 7.3-7.545(m,ArH), 7.71(s,1H, pyrazineH).

STEP 10F: trans-2-[3-n-propylsulfonyl-4-n-propoxy-5-(2-oxopropoxy) phenyl]-5-[6-(2,3-dimethoxy)pyrazyl]tetrahydrofuran The title compound was prepared from trans-2 (3-n propylsulfonyl-4-n propoxy 5-benzyloxyphenyl) -5-[6 (2,3 dimethoxy)pyrazyl]tetrahydrofuran according to procedures described in Example 1, Steps I, and Example 2. NMR (CDCl$_3$) (pertinent signals) 2.34 (s, CH$_2$COCH$_3$), 4.2(t, OCH$_2$CH$_2$CH$_3$), 4.67(s, CH$_2$COCH$_3$), 7.15, 7.54(2 br s, Ar-H), 7.7(s,pyrazine H).

EXAMPLE 11
trans-2-[3-n-propylsulfonyl-4-n-propoxy-5-(2-hydroxypropoxy) phenyl]-5-[6-(2,3-dimethoxy)pyrazyl]tetrahydrofuran The title compound was prepared from trans-2-[3-n-propylsulfonyl-4-n-propoxy-5-(2-oxopropoxy) phenyl]-5-[6-(2,3-dimethoxy)pyrazyl]-tetrahydrofuran according to procedures described in Example 3. NMR (CDCl$_3$) (pertinent signals) 0.95,1.0(2t, 6H, CH$_2$CH$_2$CH$_3$), 3.35(m,SO$_2$CH$_2$CH$_2$CH$_3$), 3.8-4.3(OCH$_3$, OCH$_2$CH(OH)CH$_3$, OCH$_2$CH$_2$CH$_3$), 5.19(m,C-2H,C 5H0, 7.21,7.46(2 br s, ArH), 7.68(s, pyrazine H).

EXAMPLE 12
trans-2-[3-(2-Hydroxypropyl)sulfonyl-4-n-propoxy-5-(2-oxopropoxy) phenyl]-5-[6-(2.3 dimethoxy) pyrazyl]tetrahydrofuran The title compound was prepared according to procedures described in Example 3. NMR (CDCl$_3$) δ 8 1.08(t, OCH$_2$CH$_2$CH$_3$), 1.28(m, SO$_2$CH$_2$CH(OH)CH$_3$), 2.35(s,CH$_2$COCH$_3$), 7.18, 7.58(2 br s, ArH), 7.71(s, pyrazine H).

EXAMPLE 13
trans-2-[3-(2-Hydroxypropyl)sulfonyl-4-n-propoxy-5-methoxyphenyl]-5[6-(2,3-dimethoxy)pyrazyl]tetrahydrofuran The title compound was prepared according to procedures described in Example 11. NMR (CDCl$_3$) (pertinent signals) 3.39 (m,SO$_2$CH$_2$CH$_2$CH$_3$), 3.91, 4.0, 4.02(3 s, OCH$_3$), 5.21(m, C 2 H, C-5 H), 7.23, 7.44(2 br s, ArH), 7.70(s, pyrazine H).

What is claimed is:

1. A compound of the following structural formula

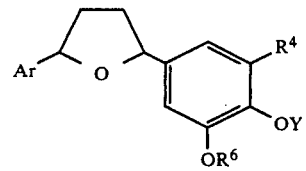

or a pharmaceutically acceptable salt thereof wherein;
Ar is selected from the group consisting of pyridyl, and 2,3-dimethoxypyridyl;
R$^4$ is S(O)$_n$ R$^2$, in which n is 0, 1 or 2, and
R$^2$ is selected from the group consisting of
  (a) C$_{2-6}$alkyl,
  (b) Substituted C$_{1-6}$alkyl wherein the substituent is selected from the group consisting of hydroxy, amino, N-C$_{1-4}$alkylamino, and N,N-di-C$_{1-4}$alkylamino, and
  (c) C$_{1-6}$alkylcarbonyl-C$_{1-6}$alkyl;
Y is selected from the group consisting of
  (a) C$_{1-12}$alkyl,
  (b) C$_{1-6}$hydroxyalkyl,
  (c) C$_{1-6}$alkoxy-C$_{1-6}$alkyl,
  (d) amino-C$_{1-6}$alkyl, and
  (e) N-substituted or N,N-disubstituted amino-C$_{1-6}$alkyl wherein the substituents are each individually C$_{1-6}$alkyl;
R$^6$ is substituted C$_{1-6}$alkyl wherein the substituent is selected from the group consisting of hydroxy, amino, N-C$_{1-4}$alkylamino, and N,N-di-C$_{1-4}$alkyamino, wherein the relationship of the substituents at positions 2 and 5 of the tetrahydrofuran includes all stereoisomers.

2. A compound of claim 1 wherein the substituents at positions 2 and 5 of the tetrahydrofuran are in a trans relationship to one another.

3. A compound according to claim 2 wherein n is 2, and R$^2$ is selected from the group consisting of:
  (a) Substituted C$_{1-6}$alkyl wherein the substituent is selected from the group consisting of hydroxy, amino, N-C$_{1-4}$alkylamino, and N,N-di C$_{1-4}$alkylamino, and
  (b) C$_{1-6}$alkylcarbonyl-C$_{1-6}$alkyl, and
Y is
  (a) C$_{1-6}$alkyl, or
  (b) C$_{1-4}$alkoxy C$_{1-4}$alkyl.

4. A compound according to claim 3 wherein Y is n-propyl or 2-oxypropyl.

5. A compound of claim 4 which is
  (a) trans-2-[3-n-propylsulfonyl-4-n-propoxy-5-(2-hydroxypropoxy) phenyl]-5-[5-(2,3-dimethoxy)-pyridyl]tetrahydrofuran,
  (b) trans-2-[3-(2-Hydroxypropyl)sulfonyl-4n-propoxy-5-(2-hydroxypropoxy) phenyl]-5[5-(2,3-dimethoxy)pyridyl]tetrahydrofuran,
  (c) trans-2[3-(2-Hydroxypropyl)sulfonyl-4n-propoxy-5-(3hydroxypropoxy) phenyl]-5[5-(2,3-dimethoxy)pyridyl]tetrahydrofuran,
  (d) trans-2-[3-(2-Hydroxypropyl)sulfonyl-4-n-propoxy-5-(3-hydroxyethoxy) phenyl]-5-[5-(2,3-dimethoxy)pyridyl]tetrahydrofuran, and
  (e) trans-2[3-(2-oxopropyl)sulfonyl-4-n-propoxy-5-(3-hydroxypropoxy) phenyl]-5-[5-(2,3-dimethoxy)-pyridyl]tetrahydrofuran, or a stereochemical isomer thereof in the (2S, 5S) configuration.

6. A pharmaceutical composition for antagonizing the effects of PAF which comprises a nontoxic therapeutically effective amount of a compound according to claim 1 and a pharmaceutically acceptable carrier.

7. A pharmaceutical composition for antagonizing the effects of PAF which comprises a nontoxic therapeutically effective amount of a compound according to claim 5 and a pharmaceutically acceptable carrier.

8. A composition of claim 7 in which the active agent is in the (2S,5S) configuration.

9. A method of antagonizing the effects of PAF in a subject in need thereof which comprises administering to said subject a nontoxic therapeutically effective amount of a compound according to claim 1.

10. A method of antagonizing the effects of PAF in a subject in need thereof which comprises administering to said subject a nontoxic therapeutically effective amount of a compound according to claim 5.

11. A method of claim 10 in which the active agent is in the (2S,5S) configuration.

* * * * *